United States Patent [19]

Zeldis et al.

[11] Patent Number: 4,952,494

[45] Date of Patent: Aug. 28, 1990

[54] ASSAY TO DETECT THE PRESENCE OF LIVE NON-A, NON-B HEPATITIS AGENTS IN VITRO

[75] Inventors: Jerome B. Zeldis, Carmichael; Robert P. Gale, Bel Air, both of Calif.; Howard N. Steinberg, Brookline, Mass.

[73] Assignee: Beth Isreal Hospital Association, Boston, Mass.

[21] Appl. No.: 280,490

[22] Filed: Dec. 6, 1988

Related U.S. Application Data

[63] Continuation-in-part of Ser. No. 175,682, Mar. 21, 1988, abandoned.

[51] Int. Cl.$^5$ .................... C12Q 1/70; C12Q 1/02; C12Q 1/18
[52] U.S. Cl. .......................... 435/5; 435/29; 435/32; 435/236; 436/820
[58] Field of Search ............ 435/5, 32, 29, 236, 435/30; 436/501, 820

[56] References Cited

U.S. PATENT DOCUMENTS 4,230,697 10/1980 Nishida et al. ..................... 514/8
4,783,407 11/1988 Provost et al. ..................... 435/235

OTHER PUBLICATIONS

Young et al, The J. of Clinical Inves., vol. 73, Jan. 1984, pp. 224–230.
Yoffe et al, The J. of Infec. Diseases, vol. 153 (3), Mar. 1986, pp. 471–477.
Zeldis et al, J. Clin. Invest. vol. 78, Aug. 1986, pp. 411–417.
Elfassi et al, PNAS U.S.A., vol. 81, 1984, pp. 3526–3528.
Lie-Injo et al, DNA, vol. 2(4), 1983, pp. 301–307.
Laure et al, Science, vol. 229, Aug. 1985, pp. 561–563.
Zeldis et al, Gastroenterology, vol. 90, May 1986, p. 1783.
Tabor et al, J. Med. Virol., vol. 11(1), 1983, pp. 1–10.
Pontisso et al, British Medical Journal, vol. 288, 26 May 1984, pp. 1563–1566.
Molecular Biology of The Cell, Alberts et al, Garland Publishing, Inc., New York & London, 1983, pp. 921–924.

Primary Examiner—Esther M. Kepplinger
Assistant Examiner—Florina B. Hoffer
Attorney, Agent, or Firm—Lorusso & Loud

[57] ABSTRACT

An assay to detect the presence of live non-A, non-B hepatitis virus in vitro. Bone marrow cells are exposed to a body fluid or biological preparation to be tested and the cells are placed in suspension. When using bone marrow cells, growth factors are added to the bone marrow stem cells. Therefore, if the number of colonies growing in the mixture are less than that number present in the culture of cells exposed to a sample that has been determined to contain no live virus, live non-A, non-B hepatitis virus is present in the sample tested. The assay is particularly useful to determine the presence of live non-A, non-B, hepatitis virus in a vaccine.

4 Claims, No Drawings

ASSAY TO DETECT THE PRESENCE OF LIVE NON-A, NON-B HEPATITIS AGENTS IN VITRO

This application is a continuation-in-part of application Ser. No. 175,682, filed Mar. 21, 1988, now abandoned.

BACKGROUND OF THE INVENTION

The present invention is a method to detect the presence of live non-A, non-B hepatitis viral agents in a sample, in a body fluid, such a serum, or in a biological preparation, such as a vaccine.

Posttransfusion non-A, non-B hepatitis (NANBH) is a serious illness. It has a disturbing tendency to progress to chronic hepatitis, even more frequently than posttransfusion type B hepatitis. Additionally, a non-A, non-B hepatitis infection is likely to be followed by an asymptomatic carrier state. More importantly, aplastic anemia is often preceded by hepatitis. It has been found that most cases of hepatitis that precede aplastic anemia are believed to be caused by non-A, non-B hepatitis viral agents. The mortality rate from aplastic anemia is quite high. The modes of transmission include transfusion, hemodialysis, renal transplantation, illicit self-injection, sexual contacts and a variety of other sources. Because of the dangers of the disease and its complications, there is an incentive to immunize susceptible populations against these viral agents much the same way immunization against smallpox, polio and hepatitis B has been accomplished.

In simplest terms, a vaccine for injection into an animal for immunization from a disease contains weakened or dead viruses. The injection of the weakened or dead virus into the animal causes natural antibodies to develop within the animal and ultimately results in an immunization by that animal toward that virus.

It is essential to the proper use of any vaccine that it does not contain any live virus that could cause disease. Of course, since the vaccine is actually made from a live virus which is either weakened or killed, there is a possibility that the vaccine might contain an infectious virus. Injecting an infectious virus into an animal would contribute toward the animal's contracting the particular disease and therefore would not accomplish the objective goal of immunization, the prevention of contraction of the disease.

Accordingly, a vaccine must be tested to determine whether or not any infectious virus is present. There is no known way to detect the presence of many infectious viruses, including hepatitis viruses, in a sample except for a very costly and time consuming use of primates. Essentially, the vaccine would be injected into a chimpanzee and after a period of time of approximately one year, if the chimpanzee did not develop the disease, the vaccine would be considered safe. This process is time consuming, as a sufficient period of time must go by to ensure that the disease does not surface in the animal. The method is also expensive as each animal used is expensive and cannot be used more than once.

Besides vaccines, humans receive a variety of blood products such as clotting factors that have been associated with transmitting diseases, such as viral hepatitis. A method to detect the presence of viral agents in these products would aid in ensuring the safety of these products for human use.

There is no way of detecting non-A, non-B hepatitis virus at this time, except to infect humans and chimpanzees. Approaches used in the past to identify hepatitis A and B antigens and viral particles have been applied unsuccessfully to the search for non-A, non-B hepatitis antigens. There are no immunological or nucleic acid probes for the virus. The only indirect markers for an infection are elevations of the aminotransferases and other liver enzymes (AST,ALT) and the exclusion of other known causes of viral hepatitis.

Recently, Young et al demonstrated that in blood of people who are diagnosed as having severe anemia (a disease which expresses itself by noticeable suppression of the growth and differentiation of bone marrow cells), a parvovirus was present which inhibited the growth and differentiation of certain bone marrow stem cells (CFU-E). Young et al developed an in vitro assay that detects the inhibition of growth of the stem cell when exposed to a sample containing the virus to indicate the presence of the virus. See N. S. Young et al, "Characterization of a Virus that Causes Transient Aplastic Crisis", *Journal of Clinical Investigation*, 73: 224–230, 1984. This parvovirus is not associated with viral hepatitis.

More recently in pending U.S. patent application Ser. No. 893,678, filed Aug. 6, 1986, entitled "Assay to Detect the Presence of Live Virus In Vitro", a method for detecting the presence of hepatitis viruses, particularly hepatitis B virus (HBV), in a sample of body fluid or in a biological preparation was disclosed. That method involved exposing mononuclear cells, derived from bone marrow or blood, in vitro to a sample to be tested for the live virus. The cells were then suspended in a semi-solid media in the presence of growth factors that promote the proliferation and differentiation of hematopoietic stem cells. After a period of time, the stem cells form a clump of cells called a colony. Depending upon the growth factors added to the cells, different types of bone marrow stem cell colonies can be detected. The number of colonies detected after exposure to hepatitis viruses is less than those present in cultures of bone marrow cells exposed to a sample that lacks the virus.

The application of these specific serological tests for the diagnosis of infection caused by hepatitis A virus (HAV) and HBV has led to the conclusion that significant numbers of cases of acute and chronic hepatitis in humans occur in the absence of infection with any known serologically identifiable virus. These cases have been tentatively designated non-A, non-B (NANB) hepatitis to indicate that the diagnosis is based on the exclusion of infection caused by HAV or HBV. The term non-A, non-B, rather than hepatitis C, was chosen to reflect the likelihood that more than one etiologic agent may ultimately be identified. Efforts to identify specific virus particles and virus antigens have been unsuccessful. In the absence of a virus-specific test for NANB hepatitis, as well as the absence of diagnostic clinical features, the diagnosis is made not only by the exclusion of HBV and HAV but also by the exclusion of Epstein-Barr virus (EBV) and cytomegalovirus (CMV). Additionally, the assays disclosed in U.S. patent application Ser. No. 893,678 (discussed above) were not successful in detecting the presence of non-A, non-B hepatitis virus in vitro; sera from chimpanzee or people infected with non-A, non-B hepatitis failed to inhibit the growth and differentiation of bone marrow stem cells. Based upon findings with HBV and subsequent data which is the subject matter of this application, the applicants have determined that the failure of NANB hepatitis virus to inhibit stem cells was caused by low titre of the virus and not a property of the virus as previously thought.

Accordingly, it is an object of the present invention to provide an assay to detect the presence of live non-A, non-B hepatitis virus in vitro.

It is another object of the present invention to provide an economic and accurate assay to detect the presence of live non-A, non-B hepatitis virus in vitro.

Still another object of the present invention is to provide an assay to detect the presence of live non-A, non-B hepatitis virus in a vaccine.

It is another object of the present invention to provide an assay for the in vitro screening of drugs and antibodies for the treatment of non-A, non-B hepatitis virus.

SUMMARY OF THE INVENTION

The present invention is an effective and economic method to detect the presence of live non-A, non-B hepatitis virus. The method comprises exposing mononuclear cells or hemopoietic derived cell lines from bone marrow or blood in vitro to a sample to be tested for live non-A, non-B hepatitis virus. The cells are then suspended in semi-solid media in the presence of growth factors that promote the proliferation and differentiation of hemopoietic stem cells. After a period of time, different types of bone marrow stem cell colonies can be detected. The number of colonies detected after exposure to non-A, non-B hepatitis virus is less than those present in cultures of bone marrow cells exposed to a sample that lacks the virus.

These and other objects of the invention will be shown from the following detailed description of the invention.

DETAILED DESCRIPTION OF THE INVENTION

It has been determined that in vitro exposure of human bone marrow to the non-A, non-B hepatitis virus results in a inhibition of the bone marrow stem cells that will ultimately differentiate into red blood cells (BFU-E, CFU-E) and granulocytes/monocytes (CFU-GM). With those findings in mind, methods have been devised to determine the presence of live non-A, non-B hepatitis viruses in vitro. One method using mononuclear cells comprises (1) exposing the mononuclear cells from bone marrow or blood in vitro to a sample that potentially contains the non-A, non-B hepatitis virs, (2) placing the mixture in suspension culture, (3) inducing the cells to differentiate and proliferate by adding growth factors and (4) determining the number of colonies present after an incubation period. If a live non-A, non-B hepatitis virus is present, the number of colonies is less than those found in cultures of cells exposed to no live non-A, non-B hepatitis virus.

Mononuclear cells are obtained from bone marrow donors who have no serologic evidence of previous or present non-A, non-B hepatitis virus infections. The mononuclear fraction of the human bone marrow cells is isolated by conventional methods, such as Ficoll-Hypaque density configuration, and subsequently suspended in cell culture media, such as RPMI-1640, which can be obtained from Grand Island Biology Corporation, Grand Island, N.Y., ("Gibco"), supplemented with fetal calf serum.

The mononuclear cells are then exposed to the samples to be tested for a predetermined period of time. Exposure of the cells to the sample, which potentially contains live non-A, non-B hepatitis virus, may occur in either of two ways. In one method, the cells are incubated with the sample for a period of time ranging from one hour to overnight, preferentially 16–24 hours. It is speculated that the non-A, non-B hepatitis virus is taken up by the cells. The cells are then washed free of extraneous non-A, non-B hepatitis virus. The cells are then suspended in semi-solid media such as plasma clot, agar, agarose or methylcellulose, using conventional techniques. See, for example, Golde D. W., Methods in Hematology: Hematopoiesis, New York, Edinburgh, London and Melbourne: Churchill Livingstone, pp. 1-361, 1984. Alternatively, the sample can be added to the cells directly and then placed in a suspension of semi-solid media for the conventional stem cell assays. The second method is preferred since that method involves less manipulation of the cells, and, accordingly, a reduced risk of exposure to infection for persons handling the samples.

When using mononuclear cells, growth factors (cytokines) specific to a particular type of stem cell are added to the suspension culture to facilitate the differentiation and proliferation of the hemopoietic stem cells so that only that type of stem cell can form a colony. The growth factors, culture conditions and guidelines for what constitutes a colony are well established hematological techniques. See, the Golde reference, discussed above. Since progenitor cells for the bone marrow cells are immobilized in a semi-solid matrix, the progeny remain within a confined area. Thus, after an appropriate incubation time (7–16 days), a colony of cells will be observed. The cells are then fixed, usually with gluteraldehyde, and stained by conventional techniques such as with the Wright-Giemsa or hematoxylin stain. The number of colonies that have grown are counted.

The number of colonies formed from cells incubated with samples that potentially contain non-A, non-B hepatitis viruses are compared to the number of colonies formed from cells incubated with a control sample that contains no non-A, non-B hepatitis virus (the control). The colonies are then counted and, if the number of colonies formed when the sample to be tested is exposed to the cells is less than the number of colonies formed when the control is mixed with the cells, it can be determined that live non-A, non-B hepatitis virus is present in the sample. The numbers of colonies when compared can be expressed as percent inhibition. That is:

$$1 - \frac{\text{the number of colonies at peak infection}}{\text{the number of colonies of control}}$$

All the data gathered is considered significant by statistical parameters. Additionally, it is believed that the extent of inhibition of colony formation may be a function of both the multiplicity of infection (m.o.i., the ratio of the number of viral particles to a cell) and the time of exposure of the cells the non-A, non-B hepatitis virus. This belief was based upon prior work on HBV and has been confirmed for HAV in an article entitled "Inhibition of In Vitro Hematopoeisis by Hepatitis A Virus" by Busch F. W.. de Vos S., et al in *Experimental Hematology* 1987; Volume 15, 978–982.

Briefly, three (3) two to four year old chimpanzees with greater than one year history of normal aminotransferases and liver biopsies were inoculated with a factor VIII concentrate (lot A 056, provided by Dr. D. Bradley) that was free of HAV and HBV and that had been implicated in transmitting NANB hepatitis or were inoculated with a factor VIII concentrate of chimpanzee plasma obtained during the peak of the viral hepatitis caused by a lot A 056. All chimpanzees developed viral hepatitis, a diagnosis based upon abnormal serum aminotransferases as well as light and electron microscopic examination of the liver histology that was read on a blind basis. Two chimpanzees, Thys and Robin, had acute self-limited hepatitis while the third, Mariska, developed histological evidence of chronic hepatic injury. Sera were obtained prior to inoculation (pre-inoculation serum), during acute liver injury (acute phase serum), after normalization of the aminotransferases and liver histology in chimpanzees Thys and Robin (recovery phase serum), and after normalization of the aminotransferases with persistent histological evidence of viral hepatitis in chimpanzee Mariska (chronic phase serum). Sera were stored at $-70°$ C. until the initial bone marrow stem cells assays were performed. All assays were conducted blindly. After recovery of the data, the identity of the serum specimens or the clinical course of the chimpanzees became known.

EXAMPLE

Bone marrow cells are obtained either from the iliac crest of normal donors or from the ribs of patients undergoing heart surgery or lung resection. Cell suspensions are prepared and are layered over Ficoll-Hypaque to separate the contaminating red blood cells and leukocytes from the desired mononuclear cells. This is achieved by spinning the cells at $400 \times$ gravity (g) for 30 minutes. The enriched mononuclear cells are washed free of the Ficoll-Hypaque, resuspended in the plating medium RPMI-1640 supplemented with 10% heat inactivated fetal calf serum and cell numbers are adjusted to the desired concentration.

The cells are then exposed to non-A, non-B hepatitis virus. $1 \times 10^6$ mononuclear cells in 0.1 ml suspension are incubated with 0.1 ml of sera containing non-A, non-B hepatitis virus that had previously caused disease in either humans or chimpanzees for 18–24 hours at $37°$ C. and an atmosphere of 5% $CO_2$. Control cells are incubated with normal human serum (Type AB blood). After infection with the non-A, non-B hepatitis virus, the bone marrow cells are washed free of extraneous non-A, non-B hepatitis virus by repeated centrifugation (10 minutes at 1500 rpm) and the addition of fresh medium to give a concentration of $1.00–3.0 \times 10^6$ cells per ml. The progenitor cells are assayed as described below.

Assay for Granulocyte-Monocyte Progenitor Cells (CFU-GM)

The granulocyte-monocyte progenitor cell (CFU-GM) is a stem cell committed or programmed to undergo proliferation and differentiation giving rise to both mature granulocytes and monocytes. These CFU-GM do not give rise to any other cell type. CFU-GM are assayed as follows:

$1 \times 10^6$ mononuclear cells are plated in either alpha medium or Iscove's Modified Dulbecco's Medium (IMDM) containing 0.3% agar (Difco, Detroit, Mich.), 20% fetal calf serum and either 10% Giant Cell Tumor Conditioned Medium (GCT) (from Gibco) or 10% phytohemagglutinin-stimulated leukocyte conditioned medium (PHA-LCM). Both GCT and PHA-LCM are a source of colony stimulating activity allowing the progenitor cells to undergo proliferation and differentiation so at the end of 10 days of culture at $37°$ C. in a 5% $CO_2$ atmosphere, discrete colonies of 40 cells or greater can be scored. PHA-LCM is prepared by the addition of 1% phytohemagglutinin (Wellcome Company, Triangle Park, N.C.) to Ficoll-Hypaque separated peripheral blood mononuclear cells. The conditioned medium is harvested after fourteen days of culture at $37°$ C. and 5% $CO_2$, sterile filtered and stored at $-20°$ C.

The results of this assay (and others) are shown on Tables 1, 2 and 3. The assay was performed on serum samples taken from chimpanzees and human donors. Sera from pre-immunized chimpanzees and humans who lack evidence of non-A, non-B hepatitis served as controls. Readings were taken for each subject at each phase of infection; (1) preinoculation, (2) peak of acute phase of infection and (3) resolving infection. The results are expressed in the mean number of colonies per $1 \times 10^5$ cells $\pm$ the standard error of the mean. The results show a decrease in the number of colonies after infection with the non-A, non-B hepatitis virus. This decrease in the number of colonies indicates that non-A, non-B hepatitis inhibits the growth of cells colonies. Therefore, the presence of non-A, non-B hepatitis virus is detected by this assay.

Assay for Mature (CFU-E) and Primitive (BFU-E) Erythroid Progenitor Cells

Both CFU-E and BFU-E are progenitor cells that are committed to differentiating into mature red blood cells. The two stem cells are distinguished by physical characteristics, their response to erythropoietin (EPO), a growth factor, and the time of their appearance in culture. Both erythroid progenitor cells may be assayed either in a methylcellulose or a plasma clot type matrix.

For methylcellulose assays, $1 \times 10^5$ mononuclear cells are cultured in IMDM in 0.8% methylcellulose, 30% fetal calf or human type AB serum, 10% PHA-LCM, $5 \times 10^{-5}$ mercaptoethanol, 1% deionized Bovine serum (Sigma, St. Louis, Mo.) and EPO. EPO is the hormone that allows both CFU-E and BFU-E to give rise to colonies of red blood cells in this culture. As CFU-E are more sensitive to the effect of EPO, only 0.1–0.3 u/ml are required to assay for CFU-E. 2 u/ml are added to cultures assaying for BFU-E. The procedure for assaying erythroid progenitor cells in plasma clot cultures is similar to the methylcellulose assay. However, beef embryo extract and Bovine citrated plasma, which can be obtained from Gibco, are substituted for the methylcellulose. For CFU-E and BFU-E, cultures were analyzed after 7 and 14 days of culture respectively. Colonies are scored as positive for erythroid cells after staining with benzidine, a specific stain for the presence of red blood cells.

Assay for the Pluripotential Progenitor Cell (CFU-GEMM)

The pluripotential stem cell is a cell more primitive than the above-described progenitor cells that are already committed to a single line of blood cell development. The CFU-GEMM are not committed to a single lineage and, in cultures, can give rise to colonies consisting of mixtures of erythroid, granulocyte-monocyte and megakaryocyte cells. The technique for assay would be similar to that described for erythroid cells except the concentration of mercaptoethanol would be $1 \times 10^{-4}$M. CFU-GEMM, however, would be scored after 16 days of culture.

Assay for CFU-T$_L$

Using the methylcellulose system, the progenitor cell (CFU-T$_L$) for T-lymphocytes, which are important in immune function, can be assayed. CFU-T$_L$ would be assayed in Alpha medium containing 20% fetal calf serum, 1% bovine serum albumin, $5 \times 10^{-5}$M mercaptoethanol and 20% interleukin 2 (Cetus Corporation, Emeryville, Calif.). Colonies would be scored after seven (7) days.

Assay for CFU-F$_N$

This progenitor gives rise to colonies of bone marrow fibroblasts that are believed to be an important component of the bone marrow architecture and appears to play a role in the differentiation of the progenitor cells outlines above. $2 \times 10^5$ bone marrow cells would be plated in suspension culture in IMDM with 15% fetal bovine serum. Colonies of fibroblasts adhering to the bottom of the culture dish would be scored after fourteen (14) days in culture.

Assay for Leukemic Cell Line Cells

Leukemic cell lines, such as K562, HL-60 and U937 have been derived from patients with leukemia and adapted for culture so that they continue to proliferate as an immortalized cell line. As cells that are abnormal counterparts of normal blood cells, they have similarly been used as tools to study the factors regulating differentiation process. Leukemic cell line cells may be infected with non-A, non-B hepatitis virus as are normal bone marrow cells. The various cell lines are readily available from a variety of laboratories such as the ATCC, and grow very well in the assays already described. Leukemic cells are harvested from stock flashes, washed twice in medium and resuspended in IMDM and 10% fetal bovine serum. Prior to culture, 30,000 leukemic cells are exposed to serum containing the virus. The mixture is incubated overnight at 37° C. in a 5% CO$_2$ atmosphere. Control cells are exposed to normal human type serum (Type AB). After culture, the cells are harvested, washed free of extraneous virus and resuspended in IMDM with 10% fetal claf serum so that the concentration of cells is approximately $3 \times 10^3$ cells/ml. The cells are then plated in plasma clot cultures so that each plasma clot culture contains 150 cells. The method for growing leukemic cells lines in plasma clot cultures has already been outlined for the growth of erythroid precursors. Colonies of leukemic cells would be scored ten (10) days after plating.

The number of colonies formed from mononuclear cells and leukemic cell line cells incubated with non-A, non-B hepatitis virus would be compared to that incubated with the normal AB+ control serum and the data expressed as the number of colonies or as percent inhibition. Each assay would be run at least in triplicate and the results reported as the mean number of colonies±-standard error of the mean and the percent inhibition of the control for each sample.

The results obtained are shown on Tables 1, 2 and 3. Five samples obtained during the acute phase of NANB hepatitis were tested. In twenty of twenty-one trials, the number of colonies formed after exposure of mononuclear cells (MNC) to acute phase sera was less than that of MNC exposed to pre-inoculation sera; twelve of the twenty had statistically significant differences (p<0.05). In the others, the number of colonies counted was too small and the variance in values too high to achieve statistical significance. In only one trial (Thys: CFU-GM, Trial 2), acute phase serum did not inhibit colony formation. Recovery or chronic serum specimens in every trial did not inhibit the number of colonies as much as acute phase sera with twelve of twenty-one trials having statistically significant differences (p<0.05).

Variations in the extent of inhibition of the various bone marrow stem cells among the trials may reflect different multiplicities of infections (m.o.i.) or the difference in the number of times the serum was freeze-thawed prior to being placed in the assay.

The tables showing the results from the blood samples of the three chimpanzees is shown below. The legends for symbols contained in all three are identical and follows Table 3. Basically, the symboles "*" (pre-inoculation to acute phase) and "#" (acute phase to recovery or chronic phase), which are in the majority, indicate statistically significant data. Whereas the symbols "+" (pre-inoculation to acute phase) and "&" (acute phase to recovery or chronic phase) indicate that the data is not statistically significant.

TABLE 1

Number of Stem Cell Colonies After Exposure to Chimpanzee Thys' Sera

| Assay or Trial # | Pre-Inoculation Serum | Acute Phase Serum #1 | Acute Phase Serum #2 | Recovery Phase Serum |
|---|---|---|---|---|
| CFU-E[a] | | | | |
| 1 | 178 ± 11 | | 107 ± 11*# | 244 ± 6 |
| 2 | 629 ± 33 | 526 ± 26*# | | 757 ± 19 |
| 3 | 123 ± 2 | 66 ± 9*# | | 152 ± 22 |
| BFU-E[b] | | | | |
| 1 | 22 ± 6 | | 14 ± 4+& | 22 ± 7 |
| 2 | 21 ± 6 | | 17 ± 3+& | 22 ± 2 |
| 3 | 39 ± 3 | 13 ± 2*# | | 46 ± 6 |
| 4 | 11 ± 1 | 10 ± 2+# | | 23 ± 4 |
| CFU-GM[c] | | | | |
| 1 | 78 ± 4 | 46 ± 1*# | | 67 ± 1 |
| 2 | 31 ± 2 | 35 ± 4+& | | 35 ± 4 |

LEGEND FOR TABLE 1
[a] number of colonies per $3.5 \times 10^4$ MNC
[b] number of colonies per $5 \times 10^4$ MNC
[c] number of colonies per $5 \times 10^4$ MNC
*the difference in the numbers of colonies between acute and pre-inoculation serum is statistically significant (p < 0.05)
+the difference in the numbers of colonies between acute and pre-inoculation serum is not statistically significant (p > 0.05)
the difference in the numbers of colonies between acute and recovery phase serum is statistically significant (p < 0.05)
&the difference in the numbers of colonies between acute and recovery phase serum is not statistically significant (p > 0.05)

In Table 1, the differences in the number of colonies in the Trials reflect the use of four different human bone marrow specimens and different lots of growth factors.

Pre-inoculation serum was obtained one week prior to inoculation with the Factor VIII preparation when the chimpanzee's liver histology and aminotransferases were normal. Acute phase sera #1 and #2 were obtained during the rise and peak of the aminotransferase elevation, respectively. Recovery phase serum was obtained after aminotransferases and liver histology normalized.

TABLE 2

Number of Stem Cell Colonies After Exposure to Chimpanzee Robin's Sera

| Assay or Trial # | Pre-Inoculation Serum | Acute Phase Serum #1 | Acute Phase Serum #2 | Recovery Phase Serum |
|---|---|---|---|---|
| CFU-E[a] | | | | |

TABLE 2-continued

Number of Stem Cell Colonies After Exposure to Chimpanzee Robin's Sera

| Assay or Trial # | Pre-Inoculation Serum | Acute Phase Serum #1 | Acute Phase Serum #2 | Recovery Phase Serum |
|---|---|---|---|---|
| 1 | 140 ± 4 | 106 ± 3*# | 119 ± 3*# | 222 ± 26 |
| BFU-E[b] | | | | |
| 1 | 19 ± 6 | 12 ± 1+& | 14 ± 4+& | 18 ± 2 |
| 2 | 17 ± 5 | 15 ± 1+& | 17 ± 3+& | 20 ± 1 |

LEGEND FOR TABLE 2
[a] number of colonies per $3.5 \times 10^4$ MNC
[b] number of colonies per $5 \times 10^4$ MNC
[c] number of colonies per $5 \times 10^4$ MNC
*the difference in the numbers of colonies between acute and pre-inoculation serum is statistically significant ($p < 0.5$)
+the difference in the numbers of colonies between acute and pre-inoculation serum is not statistically significant ($p > 0.5$)
the difference in the numbers of colonies between acute and recovery phase serum is statistically significant ($p < 0.05$)
&the difference in the numbers of colonies between acute and recovery phase serum is not statistically significant ($p > 0.05$)

In Table 2, pre-inoculation serum was obtained four months prior to inoculation with the Factor VIII preparation when the chimpanzee's liver histology and aminotransferases were normal. Acute phase sera #1 and #2 were obtained during the rise and peak of the aminotransferase elevation, respectively. Recovery phase serum was obtained after aminotransferases and liver histology normalized.

TABLE 3

Number of Stem Cell Colonies After Exposure to Chimpanzee Mariska's Sera

| Assay or Trial # | Pre-Inoculation Serum | Acute Phase Serum | Recovery Phase Serum |
|---|---|---|---|
| CFU-E[a] | | | |
| 1 | 539 ± 30 | 412 ± 6*# | 593 ± 49 |
| 2 | 171 ± 12 | 62 ± 3*# | 145 ± 7 |
| BFU-E[b] | | | |
| 1 | 27 ± 2 | 24 ± 1*# | 34 ± 1 |
| 2 | 16 ± 3 | 11 ± 1+& | 20 ± 4 |
| CFU-GM[c] | | | |
| 1 | 74 ± 6 | 43 ± 3*& | 47 ± 3 |
| 2 | 42 ± 1 | 15 ± 2*# | 31 ± 0 |

LEGEND FOR TABLE 3
[a] number of colonies per $3.5 \times 10^4$ MNC
[b] number of colonies per $5 \times 10^4$ MNC
[c] number of colonies per $5 \times 10^4$ MNC
*the difference in the numbers of colonies between acute and pre-inoculation serum is statistically significant ($p < 0.05$)
+the difference in the numbers of colonies between acute and pre-inoculation serum is not statistically significant ($p > 0.5$)
the difference in the numbers of colonies between acute and chronic phase serum is statistically significant ($p < 0.5$)
the difference in the numbers of colonies between acute and chronic phase serum is not statistically significant ($p > 0.05$)

In Table 3, the differences in the number of colonies in Trials 1 and 2 reflect the use of two different human bone marrow specimens and two different lots of growth factors. Pre-inoculation serum was obtained eight months prior to inoculation with the Factor VIII preparation when the chimpanzee's liver histology and aminotransferases were normal. Acute phase sera #1 and #2 were obtained during the peak of the aminotransferase elevation. Chronic phase serum was obtained after aminotransferases normalized but the liver histology still was abnormal.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and there is no intention to exclude an equivalents thereof. Hence, it is recognized that various modifications are possible within the scope of the present invention as claimed.

What is claimed is:

1. A method for detecting the presence of live non-A, non-B hepatitis virus in a sample of a body fluid or biological preparation comprising:
    (a) providing a source of non-A, non-B hepatitis virus free cells obtained from bone marrow or peripheral blood;
    (b) isolating mononuclear cells from the cells obtained in step (a);
    enriching the mononuclear cells with a growth factor;
    incubating the mononuclear cells with the sample to be tested under conditions which promote the proliferation of mononuclear cell colonies;
    counting the number of colonies that arise from the incubation;
    comparing the number of colonies to a control to detect the presence of live non-A, non-B hepatitis virus wherein the presence of live hepatitis virus is related to the inhibition of colony growth.

2. The method of claim 1 wherein the hepatitis bone marrow cells are obtained by aspiration from the iliac crest, from ribs or from peripheral blood of people with no serological evidence of non-A, non-B hepatitis virus infection.

3. The method of claim 1 wherein the mononuclear cells are preincubated with the sample to be tested for one hour to overnight prior to said incubating step, the cells are then washed to remove any virus which has not been taken up by the cells.

4. The method of claim 3 wherein the preincubation period is from 16–24 hours prior to the incubation step.

* * * * *

UNITED STATES PATENT AND TRADEMARK OFFICE
CERTIFICATE OF CORRECTION

PATENT NO. : 4,952,494
DATED : August 28, 1990
INVENTOR(S) : Zeldis et al.

It is certified that error appears in the above-identified patent and that said Letters Patent is hereby corrected as shown below:

Col. 3, line 49, delete "virs" and insert --virus--;

line 61, delete "configuration" and insert --centrifugation--.

Col. 8, line 53, "Pre-inoculation" should not begin a new paragraph.

Col. 9, Table 3, under LEGEND FOR TABLE 3, next to last line, before "the difference" insert --&--.

In the claims:

Col. 10, line 29, before "enriching" insert --(c)--;

line 31, before "incubating" insert --(d)--; same line, after "cells" insert --from step c--;

line 34, before "counting" insert --(e)--;

line 35, after "incubation;" insert --and--;

line 36, before "comparing" insert --(f)-- ;

lines 40-41, delete "hepatitis bone marrow";

line 41, after "cells" insert --of step (a)--

Signed and Sealed this

Twenty-second Day of September, 1992

Attest:

DOUGLAS B. COMER

*Attesting Officer*     *Acting Commissioner of Patents and Trademarks*